(12) United States Patent
Espinoza

(10) Patent No.: US 6,709,663 B2
(45) Date of Patent: Mar. 23, 2004

(54) MULTIVESICULAR EMULSION DRUG DELIVERY SYSTEMS

(75) Inventor: Robert Espinoza, San Benito, TX (US)

(73) Assignee: HealthPoint, Ltd., San Antonio, TX (US)

( * ) Notice: Subject to any disclaimer, the term of this patent is extended or adjusted under 35 U.S.C. 154(b) by 0 days.

(21) Appl. No.: 09/944,760

(22) Filed: Aug. 31, 2001

(65) Prior Publication Data

US 2003/0049281 A1 Mar. 13, 2003

(51) Int. Cl.[7] .............. A61K 7/00; A61K 7/16; A61K 7/42; A61K 7/32; A61K 7/075
(52) U.S. Cl. .............. 424/401; 424/49; 424/59; 424/65; 424/70.28; 424/400; 424/405; 424/450; 514/558; 514/642; 514/725; 514/817; 514/859; 514/865; 514/887; 514/938
(58) Field of Search .............. 424/65, 400, 401, 424/450, 405, 59, 49, 20.28; 514/558, 642, 725, 859, 817, 865, 887, 938

(56) References Cited

U.S. PATENT DOCUMENTS

| | | |
|---|---|---|
| 4,911,928 A | 3/1990 | Wallach et al. |
| 5,165,994 A | 11/1992 | Kaler et al. |
| 5,520,908 A | 5/1996 | Lundmark |
| 5,601,811 A | 2/1997 | Gallagher et al. |
| 5,679,327 A | 10/1997 | Darkwa et al. |
| 5,804,203 A * | 9/1998 | Hahn et al. .............. 424/401 |
| 5,843,193 A | 12/1998 | Hawkins et al. |
| 5,869,071 A | 2/1999 | Wieselman et al. |
| 5,871,763 A | 2/1999 | Luu et al. |
| 6,010,690 A | 1/2000 | Varco |
| 6,024,951 A | 2/2000 | Babinski et al. |
| 6,037,386 A | 3/2000 | Modak et al. |
| 6,071,535 A | 6/2000 | Hayward et al. |

* cited by examiner

Primary Examiner—Thurman K. Page
Assistant Examiner—Marina Lamm
(74) Attorney, Agent, or Firm—McKee, Voorhees & Sease, P.L.C.

(57) ABSTRACT

A topical delivery composition which employs a multivesicular emulsion in combination with a pharmaceutically/pharmacologically active agent is disclosed. The multivesicular emulsion is formed from a quaternary amine salt emulsifier such as behentrimonium methosulfate. The emulsion is multi-lamellar which is a series of concentric spheres or vesiculars of oil and water phase that can be seen microscopically. As a result, the active is time released over a sustained period rather than spike released as is common with most topicals.

16 Claims, 3 Drawing Sheets

MULTIVESICULAR EMULSION DRUG DELIVERY SYSTEMS

FIELD OF THE INVENTION

This invention relates to topical compositions having a unique multivesicular emulsion characteristic.

BACKGROUND OF THE INVENTION

Topical delivery systems are, of course, known and they run the gambit of physical characteristics from solids, to various creams of varying degrees of lubricity, to ointments and to lotions. A key for a successful topical delivery systems is, in fact, how successful they are at delivery of the so-called active. For example, with most topical actives there is a high or so-called spike release immediately after application followed by a dramatic decrease in release over time. This is not satisfactory since the initial spike dose is often too high and there is a lack of sustained release over time, resulting in minimized effectiveness. Moreover, not only is lack of sustained release and the observation of a spike release a problem, but often with spike releases, there is overdosing in spot areas which can cause skin irritation.

The topical products susceptible to both spike dosing and skin irritation can occur in a variety of physical forms, including solids, liquids, suspensions, semisolids (such as creams, gels, lotions, pastes or "sticks"), powders or finely dispersed liquids such as sprays or mists. Examples of topical products commonly classified as "cosmetics" include skin care products such as moisturizing creams and lotions, and "treatment cosmetics" such as exfoliants and/or skin cell renewal agents; fragrances such as perfumes and colognes, and deodorants; shaving-related products such as creams, "bracers" and aftershaves; depilatories and other hair removal products; skin cleansers, toners and astringents; pre-moistened wipes and washcloths; tanning lotions and sunscreens; bath products such as oils; eye care products such as eye lotions and makeup removers; foot care products such as powders and sprays; skin colorant and make-up products such as foundations, blushes, rouges eye shadows and lines, lip colors and mascaras; lip balms and sticks; hair care and treatment products such as shampoos, conditioners, colorants, dyes, bleaches, straighteners, and permanent wave products; baby products such as baby lotions, oils, shampoos, powders and wet wipes; feminine hygiene products such as deodorants and douches; skin or facial peels applied by dermatologists or cosmeticians; and others.

Examples of topical products commonly classified as "topical actives: are many and varied, and include over-the-counter and/or prescription products such as antiperspirants, insect repellants, sunscreens and sunburn treatment, anti-acne agents, antibiotics, therapeutic retinoids, anti-dandruff agents, external analgesics such as capsaicin products, topical contraceptives, topical delivery systems, suppositories and enemas, hemorrhoid treatments, vaginal treatments, lozenges, and many other products with therapeutic or other effects. Other topical products include hand, facial and body soaps and detergents and other forms of skin cleansers, as well as household detergents and many other household products such as solvents, propellants, polishes, lubricants, adhesives, waxes and others which are either applied topically or are topically exposed to the body during normal use.

This invention is useful for topical cosmetics, topical treatment cosmetics and for topical actives.

Accordingly, it is a primary objective of the present invention to provide topical delivery compositions which contain a pharmaceutically/pharmacologically active agent and which do not have the normally attended problem of spike release nor the problem of ineffective sustained release.

Importantly, the invention also relates to a method of making topical delivery compositions which assures that the emulsion containing the pharmaceutically/pharmacologically active agent will be a multivesicular emulsion as that term is defined herein.

The method and manner of accomplishing each of the above objectives as well as others will become apparent from the detailed description of the invention which follows herein after.

SUMMARY OF THE INVENTION

The present invention relates to a method of preparing a topical delivery composition and to the composition itself. The composition can be characterized as a multivesicular emulsion which may contain a pharmaceutically/pharmacologically active agent. The emulsifier, which if used in the way described herein, provides a multivesicular emulsion, is preferably a quaternary amine salt such as behentrimonium methosulfate used at a level of from 0.1% by weight of the total composition to 30% by weight of the total composition. It's preferred level is from 0.5% by weight of the total composition to 5% by weight of the total composition. In the method, the pharmaceutically/pharmacologically active agent is mixed with the most compatible phase for it (either the oil phase or the water phase) and thereafter it is high sheer mixed with a quaternary amine salt emulsifier. In addition, the pharmaceutically/pharmacologically active agent may be suspended in the emulsion where it becomes entrapped within the vesicle. In these cases, a multivesicular emulsion forms which avoids spike release and yet has long term sustained release. The composition itself surprisingly affects the biophysical properties of the skin such as increased blood flow, reduction of transepidermal water loss, and increase of skin hydration.

DETAILED DESCRIPTION OF A PREFERRED EMBODIMENT

Figure 1:
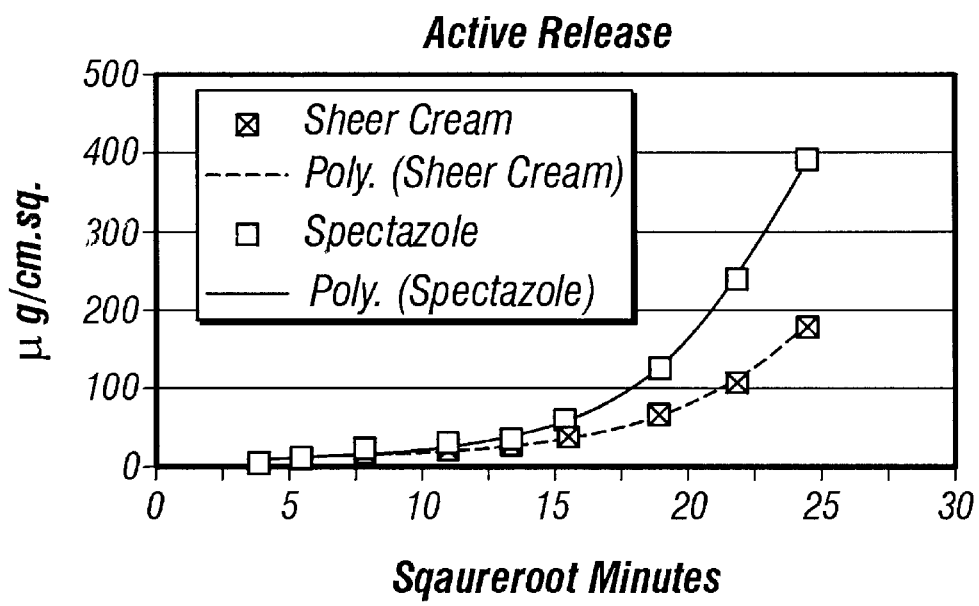
FIG. 1 shows a comparison of release rate of an antifungal drug from a conventional emulsion and the multivesicular emulsion of the present invention.

The present composition is a topical delivery composition which is characterized as a multivesicular emulsion which may contain a pharmaceutically/pharmacologically active agent.

Generally speaking, the composition is comprised of a cationic quaternary amine salt emulsifier with a fatty chain length from C12–C30, preferably C19–C26, and most preferably C22, which forms a multivesicular emulsion in an oil-in-water emulsion system. The preferred emulsifier is a quaternary amine salt derived from colza (rapeseed) oil which is high in erucic acid content. The material is specifically known as behentrimonium methosulfate. It is typically supplied in combination with cetearyl alcohol at a 25% by weight level of behentrimonium methosulfate in the secondary emulsifier known as cetearyl alcohol. Croda Inc. is a known commercially available source for behentrimonium methosulfate sold under the trademark Incroquat® Behenyl TMS. Details of the product sold under the trade name Incroquat® Behenyl TMS are described in a Jun. 1, 1994 brochure of Croda Inc. which is being supplied to the Patent Office in the Information Disclosure Statement. The composition is described in that brochure as an elegant cationic emulsion enhancing the field properties of skin care creams and conferring detangling properties for hair. There is no disclosure in that Jun. 1, 1994 brochure of the use of Incroquat Behenyl TMS in making multivesicular emulsions as made herein.

As used herein, the phrase "multivesicular emulsion" refers to a two-phase, oil-in-water emulsion system which has a multilamellar series of concentric spheres or shells of oil and water phases. It is considerably different from a micellular emulsion system consisting of droplets of an internal phase suspended in a contiguous external phase. It is also different from a multiphase emulsion which consists of single micelles of oil and water suspended in a contiguous external phase. The layers of the multivesicular emulsion can be seen microscopically and easily distinguished as alternating layers of the vesiculars. Under a microscope it looks very similar to the cross-section of an onion. As a result, the active trapped in either the alternating oil phase or the alternating water phase or entrapped within the vesicle can be time released as opposed to spike release commonly characteristic in conventional droplet emulsions.

In order to achieve the multivesicular emulsion, it is both necessary to use the correct emulsifier and to prepare the product in the correct way. Both are here described.

The quaternary amine salt is preferably behentrimonium methosulfate with the amount of the emulsifier being from 0.1% by weight of the total composition to about 30% by weight of total composition, preferably from about 0.5% by weight of the total composition to about 5% by weight of the total composition.

As earlier mentioned, the preferred emulsifier is available from Croda Inc. The behenyl quaternary surfactant is preferably behentrimonium methosulfate or behentrimonium chloride. A preferred source of behentrimonium methosulfate is INCROQUAT® Behenyl TMS (from Croda Inc.), which comprises 25% behentrimonium methosulfate. Alternatively, the surfactant may be behenalkonium chloride, dibehenyldimonium methosulfate, or behenamidopropyl ethyldimonium ethosulfate. In the form available from Croda Inc., the emulsifier for quaternary amine salt consists of a combination of behentrimonium methosulfate in cetearyl alcohol and is supplied in a easy to use pastille at 25% of behentrimonium methosulfate and 75% cetearyl alcohol. It is preferred that it is used with a fatty alcohol secondary emulsifier as supplied from Croda Inc. and preferably that emulsifier is cetearyl alcohol. The amount of secondary emulsifier should be from 1.5 times to 4 times the amount of the behentrimonium sulfate.

This emulsifier system can be used to form multivesicular emulsions in both oil and water and water in oil emulsions, although the former is more common.

The precise topically active agent used in the topical delivery composition of the present invention is not critical. In fact, pharmaceutically/pharmacologically active agents that are both water phase soluble and/or oil phase soluble may be used. As those skilled in the art of formulation know the precise percentage of the active will vary depending upon what active is, in fact, selected; but, it will generally be within the range of from about 0.01% to 15% active agent. Typical active agents can be acne actives including those for the treatment of rosacea, analgesics, anesthetics, anorectals, antihistamines, anti-inflammatory agents, antibiotics, antifungals, antivirals, antimicrobials, such as silver, silver compounds, clindamycin phosphate, erythromycin, sodium sulfacetamide, scabicides, pediculicides, antineoplastics, antiperspirants, antipruritics, antisporadics, antiseborrheics, burn actives, cauterizing agents, depigmenting agents, diaper rash agents, enzymes, hair growth actives, kerotolytics, canker sore actives, cold sore actives, dental actives, saliva actives, photosensitizing actives, steroids, sunburn actives, sunscreens, wart actives, wound treatment products, metronidazole, and retinol.

In addition to the active and the multivesicular emulsion emulsifier to the quaternary amine salt and preferably behentrimonium methosulfate, the composition may contain other excipients to provide it in various forms for specific product fields.

The topical formulations of the present invention may be prepared in a variety of physical forms. The primary product forms are solids, creams, lotions, and gels/serums. The principal differences between these forms are their physical appearance and viscosity (or thickness), which are governed primarily by the presence and amount of emulsifiers and viscosity adjusters; in fact, the main ingredients are, in many cases, common among these product forms. Moreover, a particular topical formulation may often be prepared in a variety of these forms. Solids are generally firm and non-pourable and commonly are formulated as a bar or stick, or in particulate form; solids may be opaque or transparent, and optionally may contain solvents (including water and alcohol), emulsifiers, moisturizers, emollients, fragrances, dyes/colorants, preservatives and active ingredients. Creams and lotions are often similar to one another, differing mainly in their viscosity (creams are typically thicker and more viscous than lotions); both lotions and creams may be opaque, translucent or clear and often contain emulsifiers, solvents (including water and alcohol) and viscosity adjusting agents. Lotions and creams also may optionally contain moisturizers and emollients (especially in the case of skin care products), as well as fragrances, dyes/colorants, preservatives and active ingredients. Gels/serums may be prepared with a range of viscosities, from thick (high viscosity) to thin (low viscosity) and differ principally from lotions and creams in that gels/serums are usually clear rather than opaque. Like lotions and creams, gels/serums often contain emulsifiers, solvents (including water and alcohol) and viscosity adjusters, and may also contain moisturizers and emollients, fragrances, dyes/colorants, preservatives and active ingredients.

Suitable viscosity adjusting agents (i.e., thickening and thinning agents) for use in the formulations of the present invention include, but are not limited to, protective colloids or non-ionic gums such as hydroxyethylcellulose (e.g., Cellosize HEC QP52,000-H, manufactured by Amerchol), xanthan gum, and sclerotium gum (Amigel 1.0), as well magnesium aluminum silicate (Veegum Ultra), silica, microcrystalline wax, beeswax, paraffin, and cetyl palmitate. In addition, appropriate combinations or mixtures of these viscosity adjusters may be utilized according to the present invention. A particularly preferred thickening agent for use in the formulations of the present invention, especially in the case of gels/serums, in the nonionic polymer hydroxyethylcellulose, which is compatible with strontium nitrate and is stable at pH values around 3.

Suitable solvents for use in the formulations of the present invention include, but are not limited to, water, ethanol, butylene glycol, propylene glycol, isopropyl alcohol, isoprene glycol, glycerin, Carbowax 200, Carbowax 400, Carbowax 600, and Carbowax 800. In addition, combinations or mixtures of these solvents may be used according to the present invention.

Suitable surfactants for use in the formulations of the present invention include, but are not limited to nonionic surfactants like Surfactant 190 (dimethicone copolyol), Polysorbate 20 (Tween 20), Polysorbate 40 (Tween 40), Polysorbate 60 (Tween 60), Polysorbate 80 (Tween 80), lauramide DEA, cocamide DEA, and cocamide MEA, amphoteric surfactants like oleyl betaine and cocamidopropyl betaine (Velvetex BK-35), and cationic surfactants like Phospholipid PTC (Cocamidopropyl phosphatidyl PG-dimonium chloride). Appropriate combinations or mixtures of such surfactants may also be used accordingly to the present invention. Anionic surfactants have been found to present stability difficulties when used alone in formulations containing high strontium salt concentrations.

Suitable preservatives for use in the formulations of the present invention include, but are not limited to, antimicrobials such as Germaben II (manufactured by ICI; propylene glycol, diazolidinyl urea, methylparaben, and propylparaben), methylparaben, propylparaben, imidazolidinyl urea, benzyl alcohol, sorbic acid, benzoic acid, sodium benzoate, dichlorobenzyl alcohol, and formaldehyde, as well as physical stabilizers and antioxidants such as alpha-tocopherol (vitamin E), sodium ascorbate/ascorbic acid, ascorbyl palmitate and propyl gallate. In addition, combinations or mixtures of these preservatives may also be used in the formulations of the present invention.

Suitable moisturizers for use in the formulations of the present invention include, but are not limited to, lactic acid and other hydroxy acids and their salts, glycerin, propylene glycol, butylene glycol, sodium PCA, Carbowax 200, Carbowax 400, and Carbowax 800. Suitable emollients for use in the formulations of the present invention include, but are not limited to, PPG-15 stearyl ether, lanolin alcohol, lanolin, lanolin derivatives, cholesterol, petrolatum, isostearyl neopentanoate, octyl stearate, mineral oil, isocetyl stearate, Ceraphyl 424 (myristyl myristate), octyl dodecanol, dimethicone (Dow Corning 200–100 cps), phenyl trimethicone (Dow Corning 556), Dow Corning 1401 (cyclomethicone and dimethiconol), and cyclomethicone (Dow Corning 344), and Miglyol 840 (manufactured by Huls; propylene glycol dicaprylate/dicaprate). In addition, appropriate combinations and mixtures of any of these moisturizing agents and emollients may be used in accordance with the present invention.

Suitable fragrances and colors, such as FD&C Red No. 40 and FD&C Yellow No. 5, may be used in the formulations of the present invention. Other examples of fragrances and colors suitable for use in topical products are known in the art.

Other suitable additional and adjunct ingredients which may be included in the formulations of the present invention include, but are not limited to, abrasives, absorbents, anti-caking agents, anti-foaming agents, anti-static agents, astringents (e.g., witch hazel, alcohol, and herbal extracts such as chamomile extract), binders/excipients, buffering agents, chelating agents (e.g., Versene EDTA), film forming agents, conditioning agents, opacifying agents, pH adjusters (e.g., citric acid and sodium hydroxide), and protectants. Examples of each of these ingredients, as well as examples of other suitable ingredients in topical product formulations, may be found in publications by The Cosmetic, Toiletry, and Fragrance Association (CTFA). See, e.g., *CTFA Cosmetic Ingredient Handbook*, $2^{nd}$ edition, eds. John A. Wenninger and G. N. McEwen, Jr. (CTFA, 1992).

Examples of various formulations taking advantage of the multivesicular emulsion system of the present invention, and each having various rheological properties, are set forth below.

Sample Formulations:

| Gentle Cleanser | | Hydrocortisone Cream | |
|---|---|---|---|
| Water | 77.33% | Petrolatum | 30% |
| CMT-30 | 4.0% | Lanolin Alcohol | 3% |
| Incromectant LAMEA | 5.0% | Mineral Oil | 10% |
| Methylparaben | 0.1% | Ceresin | 5% |
| Cetyl Alcohol | 3.0% | Incroquat Behenyl TMS | 2% |
| Stearyl Alcohol | 0.5% | Propylene Glycol | 3% |
| Incroquat Behenyl TMS | 5.0% | Hydrocortisone | 1% |
| Propylene Glycol | 5.0% | Water | 41% |
| Propylparaben | 0.05% | Methyl Gluceth 20 | 4% |
| Butylparaben | 0.02% | Phenoxyethanol | 1% |
| Sunscreen Lotion | | Ceramide Cream | |
| Incroquat Behenyl TMS | 3% | Sesame Oil | 4% |
| Cetyl Alcohol | 3% | Incroquat Behenyl TMS | 4% |
| Stearyl Alcohol | 1% | Cetyl Alcohol | 3% |
| Octyl Methoxycinnamate | 7.5% | Stearyl Alcohol | 1% |
| Octyl Salicylate | 5% | Macadamia Nut Oil | 1% |
| Macadamia Nut Oil | 1% | Cetiol LC | 2% |
| Avocado Oil | 1% | Avocadin | 2% |
| Sesame Oil | 4% | Crodamol OHS | 3% |
| Benzophenone 3 | 4% | Ceramide II | 0.2% |
| Water | 66.2% | Water | 71.5% |
| Glycerin | 4% | Butylene Glycol | 4% |
| Liquid Germall Plus | 0.3% | Liquid Germall Plus | 0.3% |
| | | Peach Kernal Extract | 1% |
| | | Rovisome ACE | 3% |
| Marine Botanical Cream | | Antibiotic Spray Cream | |
| Sesame Oil | 4% | Sesame Oil | 5% |
| Incroquat Behenyl TMS | 4% | Incroquat Behenyl TMS | 3% |
| Cetyl Alcohol | 3% | Cetyl Alcohol | 2% |
| Stearyl Alcohol | 1% | Stearyl Alcohol | 0.5% |
| Macadamia Nut Oil | 1% | Cetiol LC | 2% |
| Cetiol LC | 2% | Water | 83.56% |
| Avocadin | 2% | Glycerin | 3% |
| Crodamol OHS | 3% | Polymyxin B | 0.14% |
| Water | 64.7% | Neomycin Sulfate | 0.8% |
| Butylene Glycol | 4% | | |
| Liquid Germall Plus | 0.3% | | |
| Peach Kernal Extract | 1% | | |
| Rovisome ACE | 3% | | |
| Oceagen | 3% | | |
| Dermasaccharides GY | 2% | | |
| Dermasaccharides SEA | 2% | | |
| Silicone Spritz | | Zinc Oxide Spritz | |
| Water | 90.7% | Water | 73.7% |
| Incroquat Behenyl TMS | 2% | Incroquat Behnyl TMS | 2% |
| Dimethicone | 2% | Dimethicone | 2% |
| Cyclomethicone | 5% | Cyclomethicone | 5% |
| Liquid Germall Plus | 0.3% | Finsolv TN | 5% |
| | | Zinc Oxide | 12% |
| | | Liquid Germall Plus | 0.3% |
| After Shave Balm/Conditioner | | Self Tanning Cream | |
| Water | 75.5% | Incroquat Behenyl TMS | 3% |
| EnHance | 0.5% | Cetyl Alcohol | 3% |
| Glycerin | 3% | Stearyl Alcohol | 1% |
| Incroquat Behenyl TMS | 3% | Sesame Oil | 5% |

-continued

| Dimethicone | 1% | Schercemol SHS | 3% |
|---|---|---|---|
| Cyclomethicone | 5% | Propylparaben | 0.05% |
| Cetyl Alcohol | 1.5% | Water | 45.55% |
| Alcohol SD-40 | 10% | Glycerin | 4% |
| Liquid Germall Plus | 0.5% | Methylparaben | 0.8% |
| | | Sun Caps 903 | 27.6% |
| | | DNA | 4% |
| | | Erythrulose | 3% |
| AHA | | | |
| Cream w/Sunscreen | | Diaper Rash Cream | |
| Water | 63.5% | Vegelatum Equiline | 17.5 |
| Butylene Glycol | 3% | Lanolin Alcohol | 1.5% |
| Glycerin | 3% | Beeswax | 2.5% |
| Incroquat Behenyl TMS | 3% | Paraffin | 2.5% |
| Cetyl Alcohol | 2% | Incroquat Behenyl TMS | 2.5% |
| Stearyl Alcohol | 1.5% | Sesame Oil | 3% |
| Labrafil M 2130 | 2% | Sunflower Oil | 3% |
| Parsol 1789 | 3% | Water | 61.4% |
| Sesame Oil | 4% | Boric Acid | 0.1% |
| Crodamol OHS | 2% | Oatmeal | 1% |
| Octyl Methoxycinnamate | 5% | Zinc Oxide | 4% |
| Glycolic Acid | 7.5% | Phenoxyethanol | 1% |
| Liquid Germall Plus | 0.5% | | |
| | | Cream Spray | |
| Cream Spray | | w/Hydrocortisone | |
| Water | 81.5% | Water | 80.5% |
| Glycerin | 4% | Glycerin | 4% |
| Cetyl Alcohol | 3% | Cetyl Alcohol | 3% |
| Incroquat Behenyl TMS | 3.5% | Incroquat Behenyl TMS | 3.5% |
| Stearyl Alcohol | 1% | Stearyl Alcohol | 1% |
| Sesame Oil | 4% | Sesame Oil | 4% |
| Crodamol OHS | 2.5% | Crodamol OHS | 2.5% |
| Liquid Germall Plus | 0.5% | Hydrocortisone | 1% |
| | | Liquid Germall Plus | 0.5% |
| | | Cream to Powder | |
| Cream to Powder | | w/Miconazole | |
| Water | 42.5% | Water | 40.5% |
| Dimethicone | 1% | Miconazole | 2% |
| Incroquat Behenyl TMS | 2.5% | Dimethicone | 1% |
| Cyclomethicone | 9% | Cyclomethicone | 9% |
| Finsolv TN | 5% | Incroquat Behenyl TMS | 2.5% |
| Tapioca Pure | 14% | Finsolv TN | 5% |
| Dry Flo Elite | 10% | Tapioca Pure | 14% |
| Witch Hazel | 15% | Dry Flo Elite LL | 10% |
| Phenoxyethanol | 1% | Witch Hazel | 15% |
| | | Phenoxyethanol | 1% |

In each of the above formulations, it can be seen that the common characteristic is use of the Incroquat® Behenyl TMS.

As earlier mentioned, the invention is not only the selection of the proper emulsifier to form the multivesicular emulsion but also preparation in a particular way that assures multivesicular emulsion formulation. According to the method, the active is mixed with all other compatible members of its phase. By compatible members, it is meant those that it will dissolve in. For example, if the active is water soluble, it would be the water phase of the emulsion system. On the other hand, if the active is oil soluble and water insoluble, it would be mixed with the oil phase of the system. After this mixing occurs, the active and the rest of the system, i.e. the base, are then high-shear mixed with the multivesicular emulsifier such as behentrimonium methosulfate until visual inspection reveals that one does has a multivesicular emulsion. Typically, this will take from 5 to 30 minutes in a mixer such as a turbine type propeller mixer or Cowles Dissolver.

The following examples are offered to further illustrate but not limit the invention.

EXAMPLE 1

A product was prepared using a multivesicular emulsion of the present invention. In particular, the drug active was a 1% by weight suspension of econazole nitrate, a known anti-fungal drug. It was prepared with a multivesicular emulsion system of the present invention that comprised 3.5% by weight Incroquat® Behenyl TMS which was itself 25% by weight of behentrimonium methosulfate and 75% by weight of cetearyl alcohol. This was mixed with sunflower oil, cetyl alcohol, stearyl alcohol, octyl hydroxystearate, water, glycerin and the 1% by weight amount of econazole nitrate antifungal agent. After high shear mixing and inspection to confirm a multivesicular emulsion, the system had a cream appearance.

It was in this test compared with a known commercially available Johnson & Johnson product Spectazole which is an oil-in-water emulsion of the same drug. Both were tested in a diffusion cell. The results of the diffusion test revealed that there was sustained release over a period of time for the multivesicular emulsion of the present invention, but there was a spike release of short duration for the Spectazole. FIG. 1 shows the release rate data of econazole nitrate from the invention formulation and the commercially available Spectazole product in graph form.

EXAMPLE 2

Figure 2:
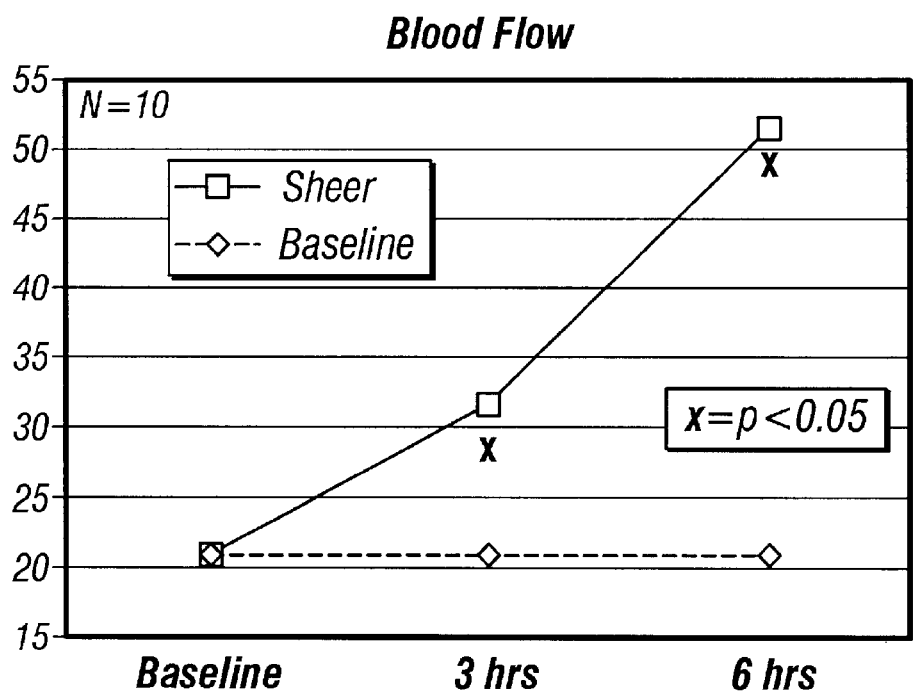
FIG. 2 shows change in peripheral blood flow for the invention.

A study with the same emulsion system of Example 1 (less the active) was conducted to investigate the product's potential to increase the peripheral blood flow when applied to the skin. A study was conducted on ten healthy subjects. A defined amount of the product was applied to the cheeks of the test subjects. Laser Doppler measurements were made to evaluate the blood flow when taken on a base line. Three and six hours after application, the results showed a significant increase in blood flow after the invention application compared to the base line. It should be noted that an increase in peripheral blood flow is equated with a better metabolic situation, an increase in cell nutrients, increase in oxygen and faster removal of cell debris and that overall an increased blood flow is essential for the healing process and for cell renewal. This test demonstrates that the multivescular system has increased blood flow in comparison with the baseline product. FIG. 2 illustrates the blood flow data in graph form.

EXAMPLE 3

This example measures the transepidermal water loss using the invention. This is an important method for accessing the efficiency of skin as a protective barrier. An increase in transepidermal water loss is always a sign of compromised skin barrier. Clinical conditions, various types of dermatitis or external factors like solvents, detergents and other irritants will increase the transepidermal loss. Good topical products should not irritate the skin. They should improve the skin's function, maintain a healthy skin and help repair a compromised skin barrier. In this example, the potential effect of the multivesicular emulsion of the present invention on the skin barrier was evaluated for the recovery rate of tape stripped skin, both treated and untreated with the invention multivesicular emulsion.

In particular, 20 healthy volunteers participated in the study. After baseline trends of epidermal water loss measurements, the skin was repeatedly taped, stripped (20 times) until the trends epidermal water loss reached a certain selected value. The multivesicular emulsion was applied to one location and additional data for epidermal water loss measurements were taken from both treated and untreated skin area.

Figure 3:
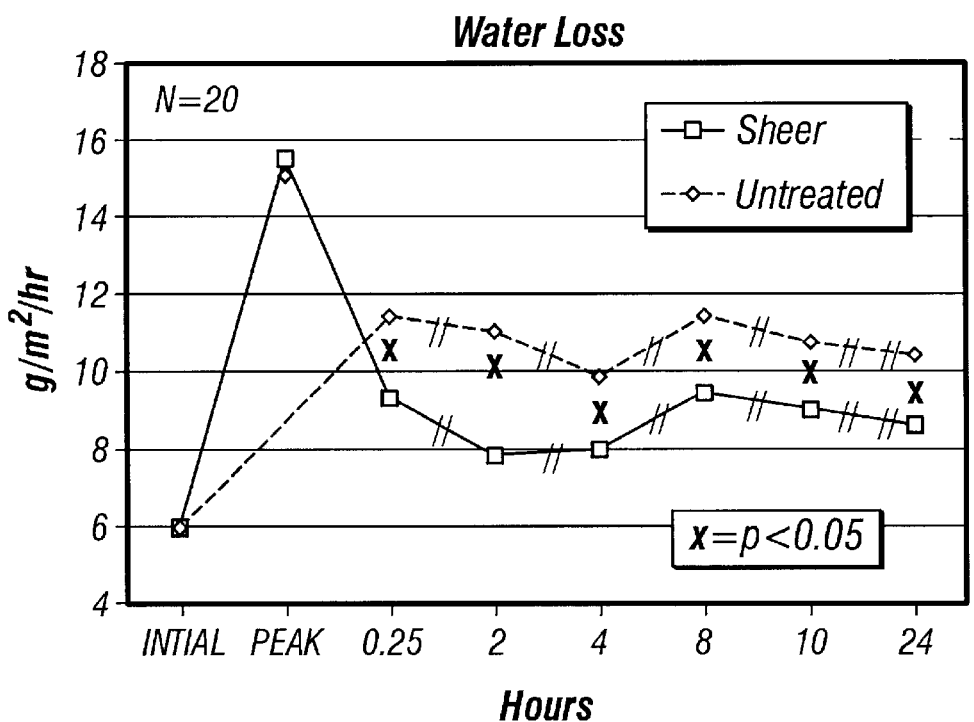
FIG. 3 shows change in transepidermal water loss for the invention.

The results are shown in FIG. 3. They demonstrate a significant reduction of transepidermal water loss. In particular, the areas treated with the multivesicular emulsion recovered significantly faster than the untreated areas.

EXAMPLE 4

Figure 4:
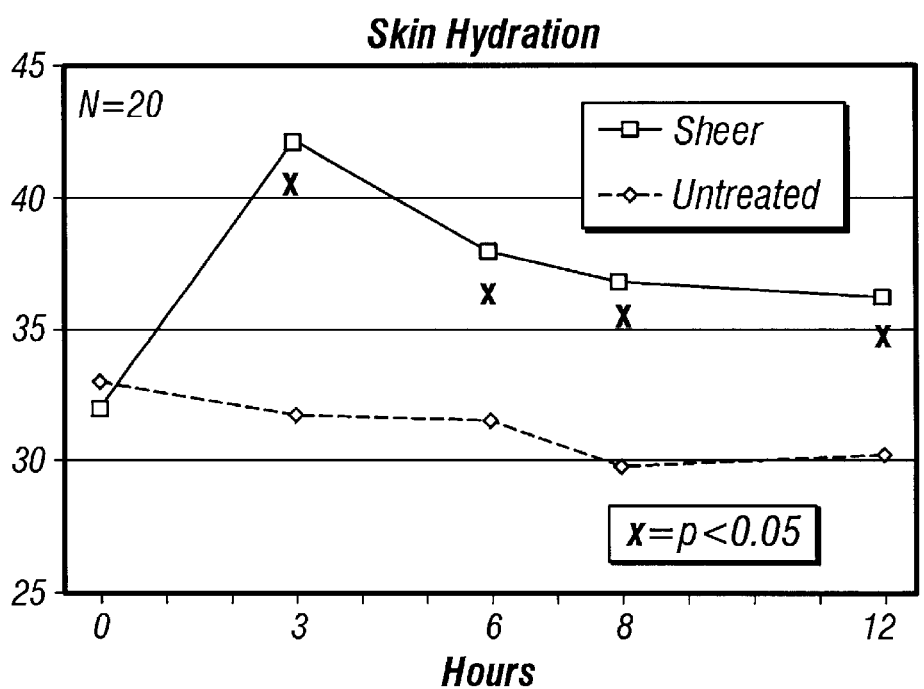
FIG. 4 shows change in skin moisture kinetics at 12 hours for the invention.
Figure 5:
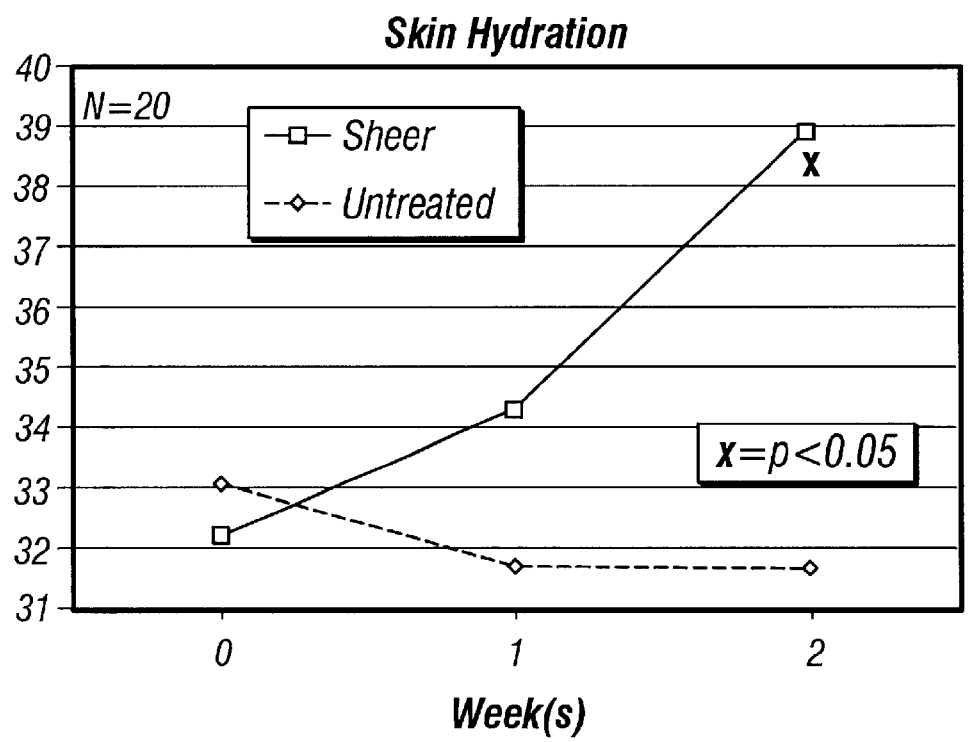
FIG. 5 shows change in skin moisture levels at two weeks for the invention.

This study was conducted to evaluate the instant and long-term moisturization effect of the multivesicular emulsion of the present invention. This system was a described in Example 1. In this test, there was an evaluation of the increase in skin hydration over a period of 12 hours and an investigation of the long-term effect in a two-week test. The results show a significant increase of skin hydration after a single application during a 12-hour time period (FIG. 4) and after twice daily application for two weeks. (FIG. 5). Even 24 hours after the last application, the skin moisture level was significantly increased indicating a long-lasting effect.

From the above studies and particularly from FIGS. 1–5, it can be seen that the multivesicular emulsion of this system avoids spike release and, in fact, is characterized by sustained release (FIG. 1). There is also a surprising increase in peripheral blood flow with respect to the areas where topical is applied (FIG. 2), there is less transepidermal water loss (FIG. 3), the system is long-lasting as evidenced by changes in skin moisture, FIG. 4 and FIG. 5 (six hours and two weeks). It, therefore, can be seen that the system accomplishes at least all of its stated objectives.

From the above description, it can be seen that the invention accomplishes at least all of its stated objectives.

What is claimed is:

1. A topical delivery composition which comprises a multivesicular emulsion consisting essentially of from 0.1% to 30% by weight of total composition of a quaternary amine salt emulsifier system and a pharmaceutically/pharmacologically active agent entrapped within the vesicles, wherein said emulsifier system is a behentrimonium methosulfate system, and wherein said multivesicular emulsion is a two-phase, oil-in-water emulsion system which has a multilamellar series of concentric spheres or shells of oil and water phases.

2. The composition of claim 1 wherein the amount of quaternary amine salt emulsifier system is from about 0.5% by weight of the total composition to about 5% by weight of the total composition.

3. The composition of claim 2, wherein the quaternary amine salt emulsifier is combined with a fatty alcohol secondary emulsifier.

4. The composition of claim 3 wherein the fatty acid alcohol secondary emulsifier is cetearyl alcohol.

5. The composition of claim 4 wherein the amount of secondary emulsifier is from 1.5 times to four times the amount of the behentrimonium sulfate.

6. The composition of claim 1, wherein the pharmaceutically/pharmacologically active agent is entrapped within the oil vesicles.

7. The topical delivery composition of claim 1, wherein the pharmaceutically/pharmacologically active agent is entrapped within the water vesicles.

8. The composition of claim 1 which includes powered excipitents.

9. The composition of claim 8 wherein the powdered excipients are selected from the group consisting of talc and corn starch.

10. The composition of claim 9 wherein the powdered excipients is talc.

11. The composition of claim 1 which includes minor ingredients selected from the group consisting of preservatives, emollients, humectants, emulsion stabilizers, water-proofing agents, skin protectants, conditioners, and fragrances.

12. The topical composition of claim 1 wherein the composition is in a delivery form selected from the group consisting of lotions, creams, sprayable creams, and creams to powder preparations.

13. The composition of claim 1 which is a semi-solid cream.

14. The composition of claim 1, wherein pharmaceutically/pharmacologically active agent is selected from the group consisting of acne actives including those for treatment of rosacea, analgesics, anesthetics, anorectals, antihistamines, anti-inflammatory agents, antibiotics, antifungals, antivirals, antimicrobials, scabicides, pediculicides, antineoplastics, antiperspirants, antipruritics, antisporadics, antiseborrheics, burn actives, cauterizing agents, depigmenting agents, diaper rash agents, enzymes, hair growth actives, kerotolytics, canker sore actives, cold sore actives, dental actives, saliva actives, photosensitizing actives, steroids, sunburn actives, sunscreens, wart actives, wound treatment products, metronidazole and retinol.

15. A method of preparing a topical delivery composition which comprises a multivesicular emulsion consisting essentially of a quaternary amine salt emulsifier system and a pharmaceutically/pharmacologically active agent entrapped within the vesicles, wherein said emulsifier system is a behentrimonium methosulfate system, and wherein said multivesicular emulsion is a two-phase, oil-in-water emulsion system which has a multilamellar series of concentric spheres or shells of oil and water phases, said method comprising: mixing the pharmaceutically/pharmacologically active agent with a compatible base which is either an oil phase or a water phase, depending upon the active and thereafter; mixing the active agent and base with from 0.1% to 30% by weight of the total composition of the quaternary amine salt emulsifier system until a multivesicular emulsion capable of timed active release is provided.

16. The method of claim 15 wherein the amount of the quaternary amine salt emulsifier system is from about 0.5% by weight of the total composition to about 5% by weight of the total composition.

* * * * *